US007122528B2

(12) United States Patent
Fahrig et al.

(10) Patent No.: US 7,122,528 B2
(45) Date of Patent: Oct. 17, 2006

(54) USE OF 5-SUBSTITUTED NUCLEOSIDES AND/OR PRODRUGS THEREOF IN THE RESISTANCE-FREE TREATMENT OF INFECTIOUS DISEASES

(75) Inventors: Rudolf Hinrich Hermann Fahrig, Hannover (DE); Denise Sonntag, Dresden (DE)

(73) Assignee: RESPROTECT GmbH, Dresden (DE)

( * ) Notice: Subject to any disclaimer, the term of this patent is extended or adjusted under 35 U.S.C. 154(b) by 60 days.

(21) Appl. No.: 10/468,017

(22) PCT Filed: Feb. 22, 2002

(86) PCT No.: PCT/EP02/01890

§ 371 (c)(1),
(2), (4) Date: Feb. 4, 2004

(87) PCT Pub. No.: WO02/067951

PCT Pub. Date: Sep. 6, 2002

(65) Prior Publication Data

US 2004/0127454 A1 Jul. 1, 2004

(30) Foreign Application Priority Data

Feb. 23, 2001 (DE) ............................... 101 08 851

(51) Int. Cl.
*A61K 31/7072* (2006.01)
(52) U.S. Cl. ....................................................... 514/50
(58) Field of Classification Search ................... 514/50
See application file for complete search history.

(56) References Cited

U.S. PATENT DOCUMENTS

| 3,287,351 | A |   | 11/1966 | Cantineau et al. |         |
|-----------|---|---|---------|------------------|---------|
| 4,656,260 | A |   | 4/1987  | Kato et al.      |         |
| 4,894,365 | A |   | 1/1990  | De Clercq et al. |         |
| 4,902,678 | A |   | 2/1990  | Smith            |         |
| 4,988,678 | A |   | 1/1991  | De Clercq et al. |         |
| 5,064,946 | A | * | 11/1991 | Shaver et al. .............. | 536/28.2 |
| 5,250,296 | A |   | 10/1993 | Ootsu            |         |
| 5,763,447 | A |   | 6/1998  | Jacobus et al.   |         |
| 5,831,064 | A |   | 11/1998 | Chang et al.     |         |
| 6,011,000 | A |   | 1/2000  | Perrine et al.   |         |
| 6,245,750 | B1|   | 6/2001  | Shepard          |         |
| 6,589,941 | B1|   | 7/2003  | Fahrig et al.    |         |

FOREIGN PATENT DOCUMENTS

| DE | 19705277 | 11/1997 |
|----|----------|---------|
| EP | 0143987  | 6/1985  |
| EP | 0488718  | 6/1992  |
| GB | 1473148  | 5/1977  |
| GB | 2310139  | 8/1997  |

OTHER PUBLICATIONS

Banker, G.S. et al, Modern Pharmaceutics, 1996, p. 596.*
David Romero et al., "Gene Amplification and Genomic Plasticity in Praokaryotes", Annu. Rev. Genet., vol. 31, pp. 91-111 (1997).
Alan F. Cowman et al., "Antifolate Drug Selection Results in Duplication and Rearrangement of Chromosome 7 . in *Plasmodium chabaudi*", Molecular and Cellular Biology, vol. 9, No. 11, pp. 5182-5188 (1989).
Alan F. Cowman et al., "Chromosomal Rearrangements and Point Mutations in the DHFR-TS Gene of *Plasmodium chabaudi* Under Antifolate Selection", Molecular and Biochemical Parasitology, vol. 42, pp. 21-29 (1990).
Manami Tanaka et al., "Mutant dihydrofolate Reductase-thymidylate Synthase Genes in Pyrimethamine-Resistant *Plasmodium falciparum* with Polymorphic Chromosome Duplications", Molecular and Biochemical Parasitology, vol. 42, pp. 83-91 (1990).
Manami Tanaka et al., "Dihydrofolate Reductase Mutations and Chromosomal Changes Associated with Pyrimethamine Resistance of *Plasmodium falciparum*", Molecular and Biochemical Parasitology, vol. 39, pp. 127-134 (1990).
Junichi Watanabe et al., "Establishing a Physical Map of Chromosome No. 4 of *Plasmodium falciparum*", Molecular and Biochemical Parasitology, vol. 65, pp. 189-200 (1994).
Simon J. Foote et al., "Amplification of Multidrug Resistance Gene in Some Chloroquine-Resistant Isolates of P. falciparum", Cell, vol. 57, pp. 921-930 (1989).
Craig M. Wilson et al., "Amplification of a Gene Related to Mammalian mdr Genes in Drug-Resistant *Plasmodium falciparum*", Science, vol. 244, pp. 1184-1186 (1989).
Alan F. Cowman et al., "Selection for Mefloquine Resistance in *Plasmodium falciparum* is Linked to Amplification of the *pfmdr1* Gene and Cross-Resistance to Halofantyrine and Quinine", Proc. Natl. Acad. Sci. USA, vol. 97, pp. 1143-1147 (1994).
M. Ouellette et al., "Drug Resistance and P-glycoprotein Gene Amplification in the Protozoan Parasite *Leishmania*", Res. Microbiol., vol. 142, pp. 737-746 (1991).
Katherine Grondin et al., "Linear Amplicons as Precursors of Amplified Circles in Methotrexate-Resistant *Leishmania tarentolae*", Nucleic Acids Research, vol. 26, No. 14, pp. 3372-3378 (1998).
Flora E. Arana et al., "Involvement of Thiol Metabolism in Resistance to Glucantime in *Leishmania tropica*", Biochemical Pharmacology, vol. 56, pp. 1201-1208 (1998).
Anass Haimeur et al., "Gene Amplification in *Leishmania tarentoae* Selected for Resistance to Sodium Stibogluconate", Antimicrobial Agents and Chemotherapy, vol. 42, No. 7, pp. 1689-1694 (1998).
Christoph Kündig et al., "role of the Locus and of the Resistance Gene on Gene Amplification Frequency in Methotrexate Resistant *Leishmania tarentolae*" Nucleic Acids Research, vol. 27, No. 18, pp. 3653-3659 (1999).

(Continued)

*Primary Examiner*—Shaojia A. Jiang
*Assistant Examiner*—Ganapathy Krishnan
(74) *Attorney, Agent, or Firm*—Greenblum & Bernstein, P.L.C.

(57) ABSTRACT

The present invention relates to the use of 5-substituted nucleosides and/or the prodrugs thereof together with at least one active substance in order to produce a drug or combination preparation for resistance-free therapy of infectious diseases caused by bacteria or protozoa.

18 Claims, 10 Drawing Sheets

OTHER PUBLICATIONS

S.N. Pancheva, "Methotrexate Potentiates Anti-Herpes Simplex Virus Type I Activity of E-5(2-Bromovinyl)-2'-Deoxyuridine", Acta Virologica, vol. 39, pp. 117-119 (1995).

Chakrabartty et al., "Loss of Plasmid Linked Drug Resistance After Treatment with Iod-deoxyuridine", Indian Journal of Experimental Biology, vol. 22, pp. 333-334 (1984).

S. Locarnini, "Hepatitis B Antiviral Therapy", Today's Life Science, vol. 2, No. 9pp. 32, 34, 36-38 and 80 (1990).

Wildiers, "Oral (E)-5-(2-Bromovinyl)-2'-Deoxyuridine Treatment of Severe Herpres Zoster in Cancer Patients", European Journal of Cancer & Clinical Oncology, vol. 20, pp. 471-476 (1984).

Chi et al., "Iododeoxyuridine Chemosensitization of cis-Diamminedichloroplatinum(II) in Human Bladder Cancer Cells", Cancer Research, vol. 54, pp. 2701-2706 (1994).

Wroblewski et al., "The Possible role of Altered Nucleotide Metabolism in Cisplatin Resistance", J. Cell Pharmacol., vol. 1, pp. 2-7 (1990).

Hirohashi et al., "Genetic Alterations in Human Gastric Cancer", Cancer Cells, vol. 3, pp. 49-52 (1991).

Sasano et al., Protooncogene Amplification and Tumor Ploidy in Human Ovarian Neoplasms, Human Pathology, vol. 21, pp. 382-391 (1990).

Borg et al., "c-myc Amplification is an Independent Prognostic Factor in Postmenopausal Breast Cancer", Int. J. Cancer, vol. 51, pp. 687-691 (1992).

Borg et al., "Association of INT2/HST1 Coamplification in Primary Breast Cancer with Hormone-Dependent Phenotype and Poor Prognosis", Br. J. Cancer, vol. 63, pp. 136-142 (1991).

Descotes et al., "Human Breast Cancer: Correlation Study Between HER-2/neu Amplification and Prognostic Factors in an Unselected Population", Anticancer Research, vol. 13, pp. 119-124 (1993).

Klijn et al., "The Clinical Significance of Epidermal Growth Factor Receptor (EGF-R) in Human Breast Cancer: A Review on 5232 Patients", Endocrine Reviews, vol. 13, pp. 3-17 (1992).

Tsuda et al., "High Incidence of Coamplification of hst-1 and int-2 Genese in Human Esophageal Carcinomas", Cancer Research, vol. 49, pp. 55505-55508 (1989).

Kennedy, "Prevention of Carcinogenesis by Protease Inhibitors", Cancer Research (Suppl.), vol. 54, pp. 1999s-2005s (1994).

Troll et al., "Trumorigenesis in Mouse Skin: Inhibition by Synthetic-Inhibitors of Proteases", Science, vol. 169, pp. 1211-1213 (1970).

Moscow et al., "Multidrug Resistance", Journal of the National Cancer Institute, vol. 80, pp. 14-20 (1988).

Oshiro et al., "Genotoxic Properties of (E)-5-(2-Bromovinyl)-2'-deoxyuridine (BVDU)", Fundamental and Applied Toxicology, vol. 18, pp. 491-498 (1992).

Iigo et al. Jpn. J. Cancer Res., vol. 81, pp. 431-435 (1990).

Sharon B. Bordow, et al., "Expression of the Multidrug Resistance-Associated Protein (MRP) Gene Correlates with Amplification and Overexpression of N-myc Oncogene in Childhood Neuroblastoma", Cancer Research, vol. 54, pp. 5036-5040 (Oct. 1994).

Alok Bhushan, et al., "Expression of c-fos in Human and Murine Multidrug-Resistant Cells", Molecular Pharmacology, 42, pp. 69-74 (1992).

Alok Bhushan, et al., "Expression of c-fos Precedes MDR3 in Vincristine and Adriamycin Selected Multidrug Resistant Murine Erythroleukemia Cells", Biochemical and Biophysical Research Communications, 226, pp. 819-821 (1996).

Thomas Braun, et al., "Differential Expression of Myogenic Determination Genes in Muscle Cells: Possible Autoactivation by the Myf Gene Products", EMBO Journal, vol. 8, No. 12, pp. 3617-3625 (1989).

Rudolf Fahrig, "Anti-Recombinogenic and Convertible Co-Mutagenic Effects of (E)-5-(2-bromovinyl)-2'-deoxyuridine (BVDU) and Other 5-substituted Pyrimidine Nucleoside Analogs in S. cerevisiae MP1", Mutation Research, 372, pp. 133-139 (1996).

Rudolf Fahrig, et al., "Induction or Suppression of SV40 Amplification by Genotoxic Carcinogens, Non-Genotoxic Carcinogens or Tumor Promoters", Mutation Research, 356, pp. 217-224 (1996).

Roy A. Frye, et al., "Detection of Amplified Oncogenes by Differential Polymerase Chain Reaction", Oncogene, 4, pp. 1153-1157 (1989).

Michael M. Gottesman, "How Cancer Cells Evade Chemotherapy: Sixteenth Richard and Hinda Rosenthal Foundation Award Lecture", Cancer Research, 53, pp. 747-754 (1993).

A.V. Gudkov, et al., "Karyotype and Amplicon Evolution During Stepwise Development of Multidrug Resistance in Djungarian Hamster Cell Lines", in I.B. Roninson (ed.), Molecular And Cellular Biology Of Multidrug Resistance In Tumor Cells, pp. 147-168 (Plenum, New York 1991).

Robert H. Haynes, "Molecular Mechanisms in Genetic Stability and Change: The Role of Deoxyribonucleotide Pool Balance", in F.J. de Serres (Ed.), Genetic Consequences Of Nucleotide Pool Imbalance, pp. 1-23 (Plenum, New York 1985).

Stephen I-Hong Hsu, et al., "Differential Overexpression of Three mdr Gene Family Members in Multidrug-resistant J774.2 Mouse Cells", Journal of Biological Chemistry, vol. 264, No. 20, pp. 12053-12062 (1989).

Stephen I-Hong Hsu, et al., "Structural Analysis of the Mouse mdrla (P-Glycoprotein) Promoter Reveals the Basis for Differential Transcript Heterogeneity in Multidrug-Resistant J774.2 Cells", Molecular and Cellular Biology, vol. 10, No. 7, pp. 3596-3606 (1990).

Bernard A. Knuz, et al., "Deoxyribonucleoside Triphosphate Levels: A Critical Factor in the Maintenance of Genetic Stability", Mutation Research, 318, pp. 1-64 (1994).

Akira Nakagawara, et al., "Inverse Correlation Between Expression of Multidrug Resistance Gene and N-myc Oncogene in Human Neuroblastomas", Cancer Research, 50, pp. 3043-3047 (1990).

Murray D. Norris, et al., "Expression of the Gene for Multidrug-Resistance—Associated Protein and Outcome in Patients with Neuroblastoma", New England Journal of Medicine, vol. 334, No. 4, pp. 231-237 (1996).

W. Ostertag, et al., "Duplicated ∝-Chain Genes in Hopkins-2 Haemoglobin of Man and Evidence for Unequal Crossing Over Between Them", Nature New Biology, 237, pp. 90-94 (1972).

András Schaefer, et al., "Decreased Resistance to N,N-dimethylated Anthracyclines in Multidrug-Resistant Friend Erythroleukemia Cells", Cancer Chemotherapy and Pharmacology, 31, pp. 301-307 (1993).

Robert T. Schimke, et al., "Overreplication and Recombination of DNA in Higher Eukaryotes: Potential Consequences and Biological Implications", Proc. Natl. Acad. Sci., 83, pp. 2157-2161 (1986).

Fredric C. Vokert, et al., "Site-Specific Recombination Promotes Plasmid Amplification in Yeast", Cell, 46, pp. 541-550 (1986).

Geoffrey M. Wahl, "The Importance of Circular DNA in Mammalian Gene Amplification", Cancer Research, 49, pp. 1333-1340 (1989).

Petra Winkelmeier, "Quantification of Cytotoxicity by Cell Volume and Cell Proliferation", ATLA, 21, pp. 269-280 (1993).

John Brennan, et al., "myc Family DNA Amplification in 107 Tumors and Tumor Cell Lines from Patients with Small Cell Lung Cancer Treated with Different Combination Chemotherapy Regimens", Cancer Research, 51, pp. 1708-1712 (1991).

Claude Desgranges, et al., "Regeneration of the Antiviral Drug (E)-5-(2-bromovinyl)-2'-deoxyuridine in vivo", Nucleic Acids Research, vol. 12, No. 4, pp. 2081-2090 (1984).

Jan Olgemöller, et al., "Determination of (E)-5-(2-bromovinyl)-2'-deoxyuridine in Plasma and Urine by Capillary Electrophoresis", Journal of Chromatography B, 726, pp. 261-268 (1999).

E. de Clercq, et al., "Pharmacokinetics of E-5-(2-Bromovinyl)-2'-Deoxyuridine in Mice", Antimicrobial Agents and Chemotherapy, vol. 16, No. 2, pp. 234-236 (1979).

Anne Livingstone, et al., "N-myc Amplification and its Relationship to Experimental Therapy", Journal of Neuro-Oncology, 31, pp. 33-39 (1997).

Pulivarthi H. Rao, et al., "Chromosomal Amplification Is Associated with Cisplatin Resistance of Human Male Germ Cell Tumors", Cancer Research, 58, pp. 4260-4263 (1998).

Alex d. Lewis, et al., "Amplification and Increased Expresion of Alpha Class Glutathione S-transferase-encoding Genes Associated with Resistance to Nitrogen Mustards", Proc. Natl. Acad. Sci., 85, pp. 8511-8515 (1988).

Tamar Kleinberger, et al., "Carcinogen-Mediated Methotrexate Resistance and Dihydrofolate Reductase . Amplification in Chinese Hamster Cells", Molecular and Cellular Biology, vol. 6, No. 6, pp. 1958-1964 (1986).

Erich Gebhart, et al., "Cytogenetic Studies on Human Breast Carcinomas", Breast Cancer Research and Treatment, 8, pp. 125-138 (1986).

Bernard Dutrillaux, et al., "Characterization of Chromosomal Anomalies in Human Breast Cancer: A Comparison of 30 Paradiploid Cases with Few Chromosome Changes", Cancer Genet Cytogenet, 49, pp. 203-217 (1990).

Xin-Yuan Guan, et al., "Identification of Cryptic Sites of DNA Sequence Amplification in Human Breast Cancer by Chromosome Microdissection", Nature Genetics, 8, pp. 155-161 (1994).

Martine Muleris, et al., "Detection of DNA Amplification in 17 Primary Breast Carcinomas With Homogeneously Staining Regions by a Modified Comparative Genomic Hybridization Technique", Genes, Chromosomes and Cancer, 10, pp. 160-170 (1994).

Joyce L. Hamlin, et al., "The Mammalian Dihydrofolate Reductase Locus", Biochimica et Biophysica Acta, 1087, pp. 107-125 (1990).

M. Kashani-Sabet, et al., "Detection of Drug Resistance in Human Tumors by *in Vitro* Enzymatic Amplification", Cancer Research, 48, pp. 5775-5778 (1988).

Gian Paolo Tonini, et al., "Antiblastic Treatment does not Affect N-myc Gene Amplification in Neuroblastoma", Anticancer Research, 7, pp. 729-732 (1987).

Akira Nakagawara, et al., "Inverse Correlation Between Expression of Multidrug Resistance Gene and N-myc Oncogene in Human Neuroblastomas", Cancer Research, 50, pp. 3043-3047 (1990).

Sharon B. Bordow, et al., "Expression of the Multidrug Resistance-associated Protein (MRP) Gene Correlates with Amplification and Overexpression of the N-myc Oncogene in Childhood Neuroblastoma", Cancer Research, 54, pp. 5036-5040 (1994).

Mohammed Kashani-Sabet, et al., "Differential Oncogene Amplification in Tumor Cells from a Patient Treated with Cisplatin and 5-Fluorouracil", Eur. J. Cancer, vol. 26, No. 3, pp. 383-390 (1990).

Marshall D. Sklar, et al., "Modulation of cis-Platinum Resistance in Friend Erythroleukemia Cells by c-myc", Cancer Research, 51, pp. 2118-2123 (1991).

Hiroyuki Yamazaki, et al., "Oncogene Overexpression and De Novo Drug-Resistance in Human Prostate Cancer Cells", Biochimica et Biophysica Acta, 1226, pp. 89-96 (1994).

Åke Borg, et al., "ERBB2 Amplification is Associated with Tamoxifen Resistance in Steroid-Receptor Positive Breast Cancer", Cancer Letters, 81, pp. 137-144 (1994).

Hyung Ju C. Shin, et al., "Study of Multidrug Resistance (mdr1) Gene in Non-Small-Cell Lung Cancer", Anticancer Research, 12, pp. 367-370 (1992).

Anna B. Hill, et al., "Increased Gene Amplification in L5178Y Mouse Lymphoma Cells with Hydroxyurea-induced Chromosomal Aberrations", Cancer Research, 44, pp. 5050-5057 (1985).

Rudolf Fahrig, "Evidence that Induction and Suppression of Mutations and Recombinations by Chemical Mutagens in S. *cerevisiae* During Mitosis are Jointly Correlated", Molec. gen. Genet., 168, pp. 125-139 (1979).

Rudolf Fahrig, "Genetic Mode of Action of Cocarcinogens and Tumor Promoters in Yeast and Mice", Molec. gen. Genet., 194, pp. 7-14 (1984).

Masamitsu Honma, et al., "Recombinagenic Activity of the Phorbol Ester 12-O-tetradecanoylphorbol-13-acetate in Human Lymphoblastoid Cells", Carcinogenesis, vol. 16, No. 8, pp. 1717-1722 (1995).

Pawan K. Gupta, et al., "High Frequency *in Vivo* Loss of Heterozygosity Is Primarily a Consequence of Mitotic Recombination", Cancer Research, 57, pp. 1188-1193 (1997).

Pascale Bertrand, et al., "Increase of Spontaneous Intrachromosomal Homologous Recombination in Mammalian Cells Expressing a Mutant p53 Protein", Oncogene, 14, pp. 1117-1122 (1997).

Kristin L. Mekeel, et al., "Inactivation of p53 Results in High Rates of Homologous Recombination", Oncogene, 14, pp. 1847-1857 (1997).

Rudolf Fahrig, "Anti-Mutagenic Agents are also CO-Recombinogenic and can be Converted into Co-Mutagens", Mutation Research, 350, pp. 59-67 (1996).

Tapio Visakorpi, et al., "*In vivo* Amplification of the Androgen Receptor Gene and Progression of Human Prostate Cancer", Nature Genetics, 9, pp. 401-406 (1995).

Pasi Koivisto, et al., "Androgen Receptor Gene Amplification: A Novel Molecular Mechanism for Endocrine Therapy Resistance in Human Prostate Cancer", Scand. J. Clin. Lab. Invest., 56, Suppl. 226, pp. 57-63 (1996).

Rudolf Fahrig, "Effects of Bile Acids on the Mutagenicity and Recombinogenicity of Triethylene Melamine in Yeast Strains MP1 and D61.M", Arch. Toxicol., 60, pp. 192-197 (1987).

J. Wildiers, et al., "Oral (E)-5-(2-Bromovinyl)-2'-Deoxyuridine Treatment of Severe Herpes Zoster in Cancer Patients", Eur. J. Cancer Clin. Oncol., vol. 20, No. 4, pp. 471-476 (1984).

Y. Benoit, et al., "Oral BVDU Treatment of Varicella and Zoster in Children with Cancer", Eur. J. Prediatr., 143, pp. 198-202 (1985).

Jose Russo, et al., "Biology of Disease: Comparative Study of Human and Rat Mammary Tumorigenesis", Laboratory Investigation, vol. 62, No. 3, pp. 244-278 (1990).

Stefan Joos, et al., "Detection of Amplified DNA Sequences by Reverse Chromosome Painting Using Genomic Tumor DNA as Probe", Human Genetics, 90, pp. 584-589 (1993).

Anne Kallioniemi, et al., "Comparative Genomic Hybridization for Molecular Cytogenetic Analysis of Solid Tumors", Science, 258, pp. 818-821 (1992).

Olli-P. Kallioniemi, et al., "Optimizing Comparative Genomic Hybridization for Analysis of DNA Sequence Copy Number Changes in Solid Tumors", Genes, Chromosomes and Cancer, 10, pp. 231-243 (1994).

Roland Kappler, et al., "Comparative Genomic *in Situ* Hybridization Discloses Chromosomal Copy Number Changes in a Transplanted Brain Tumor Line of the Rat", Mammalian Genome, 9, pp. 193-197 (1998).

Roland Kappler, et al., "Chromosomal Imbalances and DNA Amplifications in SV40 Large T Antigen-Induced Primitive Neuroectodermal Tumor Cell Lines of the Rat", Carcinogenesis, vol. *20*, No. 8, pp. 1433-1438 (1999).

M. Volm, et al., "Time Course of MDR Gene Amplification During in Vivo Selection for Doxorubicin-Resistance . and During Reversal in Murine Leukemina L 1210", AntiCancer Research, 11, pp. 579-586 (1991).

Robert T. Schimke, "Gene Amplification, Drug Resistance, and Cancer", Cancer Research, 44, pp. 1735-1742 (1984). Applicants note that pp. 1736 and 1738.

Murray D. Norris, et al., "Expression of the Gene for Multidrug-Resistance-Associated Protein and Outcome in Patients with Neuroblastoma", MRP Gene Expression and Prognosis in Neuroblastoma, vol. 334, No. 4, pp. 231-238 (Jan. 1996).

M. Volm, et al., "Time Course of MDR Gene Amplification During *in Vivo* Selection for Doxorubicin-Resistance and During Reversal in Murine Leukemia L 1210", Anticancer Research, 11, pp. 579-585 (1991).

Piotr Chomczynski, et al., "Single-Step Method of RNA Isolation by Acid Guanidinium Thiocyanate-Phenol-Chloroform Extraction", Analytical Biochemistry, 162, pp. 156-159 (1987).

James M. Ford, et al., "Pharmacology of Drugs that Alter Multidrug Resistance in Cancer", Pharmacological Reviews, vol. 42, No. 3, pp. 155-199 (1990).

A. Livingstone, et al., "N-myc Gene Copy Number in Neuroblastoma Cell Lines and Resistance to Experimental Treatment", European Journal of Cancer, vol. 30A, No. 3, pp. 382-389 (1994).

Michieli et al., "mdr-1 Gene Amplification in Acute Lymphoblastic Leukaemia Prior to Antileukaemic Treatment", Br. J. Haematol., vol. 78, pp. 288-289 (1991).

Lavi, "Carcinogen-mediated Amplification of viral DNA Sequences in Simian Virus 40-Transformed Chinese Hamster Embryo Cells", Proc. Natl. Acad. Sci, vol. 78, No. 10, pp. 6144-6148 (1981).

Demidova et al., "Gene Amplification in Murine Leukemia Cells with Multiple Drug Resistance Acquired in vivo", Genetika, vol. 23 (10), pp. 1797-1806 (1987), accompanied by an English Language Abstract.

Liu, "Oncogene Expression in Adriamycin and Platinum Resistant Cell Lines", Chung Hua I Hseuh Tsa Chih, vol. 73, pp. 552-554 (1993), accompanied by an English Language Abstract.

English language abstract of S.N. Pancheva, "Methotrexate Potentiates Anti-Herpes Simplex Virus Type 1 Activity of E-5-(2-bromovinyl)-2'-deoxyuridine", Acta Virol. (Engl. Ed.) vol. 39, No. 2, pp. 117-119 (1995).

English language abstract of H.J. Keizer et al., "Inhibition of Fluorouracil Catabolism in Cancer Patients by the Antiviral Agent (E)-5-(2-bromovinyl)-2'-deoxyuridine", Journal of Cancer Research and Clinical Oncology vol. 120, No. 9, pp. 545-549 (1994).

English language abstract of M. Iigo et al., "Optimal Treatment Regimens for 5'-deoxy-5-fluorouridine, with or without (E)-5-(2-bromovinyl)-2'-deoxyuridine, Against Various Tumors in Mice", Japanese Journal of Cancer Research, vol. 81, No. 4, pp. 431-435 (1990).

English Language Abstract of DE 197 05 277.

* cited by examiner

Inhibition of resistance development/adaptation of *E. coli* J53 (RP4) to Kanamycin by BVDU. 10 parallel batches respectively in 10 ml NB medium were evaluated.

Comparison of the minimum inhibitory concentrations (MIC) of Kanamycin with differently resistant/adapted *E. coli* J53 strains (1 × preculture in addition-free NB medium).

Comparison of the minimum inhibitory concentrations (MIC) of Kanamycin with differently adapted *E. coli* J53 strains (2 x preculture in addition-free NB medium).

Inhibition of resistance development/adaptation of *E. coli* J53 (RP4) to Amikacin by BVDU. 3 - 4 parallel batches respectively in 10 ml NB medium were evaluated.

Comparison of the minimum inhibitory concentrations (MIC) of Amikacin with differently adapted *E. coli* J53 strains (2 x preculture in addition-free NB medium).

Determination of the MIC of Kanamycin relative to an *E. coli* J53 (RP4) strain, which developed no stable resistance to 64 μg/ml Kanamycin in the presence of BVDU (1 μg/ml). With BVDU preculture, small quantities of BVDU were transferred into the MIC batches with the inoculum (5%) (final concentration: 0.04 μg/ml)

Determination of the MIC of Amikacin relative to an *E. coli* J53 (RP4) strain, which developed no stable resistance to 0.25 µg/ml Amikacin in the presence of BVDU (2 µg/ml). With BVDU preculture, small quantities of BVDU were transferred into the MIC batches with the inoculum (final concentration: 0.05 µg/ml).

Fig. 10

BVDU alone has no effect on L. donovanii. The average value from three single tests is shown.

USE OF 5-SUBSTITUTED NUCLEOSIDES AND/OR PRODRUGS THEREOF IN THE RESISTANCE-FREE TREATMENT OF INFECTIOUS DISEASES

DESCRIPTION OF BACKGROUND INFORMATION

Resistance development relative to treatment with medicines represents a universal defense mechanism of microorganisms, animals and plants. In humans, this defence mechanism is found in tumors. Generally, multiplication (amplification) of specific genes leads to the development of resistance. This gene amplification causes the overproduction of a gene product that directly or indirectly reduces the effect of the drug. Resistance development of *Plasmodia* (pathogens of malaria), and *Leishmania* (flagellates as pathogens of cutaneous Leishmaniose i.a.) is based partly on the amplification of the same genes as in human tumors.

Proof that gene amplification in bacteria leads to resistances has been successful with *Proteus* bacteria, *Escherichia coli*, *Streptococca* and *Staphylococca*. All are important hospitalism germs and pathogens of urinary tract infections (Romero and Palacios, gene amplification and genome plasticity in procaryotes, Ann. Rev. Genet. 1997). The mechanism underlying gene amplification, recombination, can likewise lead to the development of resistance. This form of resistance development has been proved unequivocally without exception in all types of bacteria but also for human tumors and all organisms which have been examined to date.

Malaria is a collective term for infections by protozoa of the *Plasmodium* type. Due to increasing resistance of *Plasmodia* to chemotherapeutics and of *Anopheles* mosquitoes to insecticides, the situation is increasingly deteriorating. Both resistances can be caused by gene amplification/recombination.

4-aminoquinolines (Chloroquine, Amodiaquine, mepacrine and Sontaquine are used as antimalaria drugs. These are analogues of quinine. Furthermore, there are two groups of antifolates, on the one hand dihydrofolate reductase (DHFR) inhibitors (pyrimethamine and chloroguanide) and on the other hand the sulphones and sulphonamides. Resistances can therefore arise due to amplification of the DHFR gene (Cowman and Lew, 1989; Cowman and Lew, 1990; Tanaka et al., 1990a; Tanaka et al. 1990b; Watanabe and Inselburg, 1994). The amplification of "Multi-drug-resistance" genes is likewise of importance (Foote et al., 1989). The amplification of the pfmdr1 gene is connected for example to resistance to mefloquine, halofantrine and quinine (Wilson et al., 1989; Cowman et al., 1994). As a result of increasing resistance of the *Plasmodia* to chemotherapeutics and *Anopheles* mosquitoes to insecticides, the situation is increasingly deteriorating. Both resistances can be caused by gene amplification/recombination. The development of resistance of *Plasmodia* is intended to be prevented by the prevention of chemotherapy-induced gene amplification.

*Leishmaniases* are caused by *Leishmania* (intracellular parasitic protozoa of the Mastigophora class) and infectious diseases transmitted by Phlebotoma (sand mosquitoes). Resistances to a chemotherapy are based on the amplification of some genes which also play a role in chemoresistance of tumours (Ouellette and Borst, 1991; Grondin et al., 1998; Arana et al., 1998; Heimeur and Ouellette, 1998; Kundig et al., 1999). The development of resistance is intended to be prevented by preventing chemotherapy-induced gene amplification/recombination.

The use of 5-substituted nucleosides for inhibiting resistance development during cytostatic treatment is already known from DE 195 45 892.

SUMMARY OF THE INVENTION

It is therefore the object of the present invention to make possible a resistance-free treatment of infectious diseases caused by bacteria or protozoa.

In one aspect, the present invention is directed to a method for the resistance-free therapeutic treatment of infectious disease caused by bacteria or protozoa, comprising administering to an individual in need thereof at least one of a 5-substituted nucleoside and a prodrug thereof together with at least one active substance.

The at least one of a 5-substituted nucleoside and prodrug thereof and the active substance can be present in a single formulation.

The at least one of a 5-substituted nucleoside and prodrug thereof and the active substance can be present in separate formulations.

(E)-5-(2-bromovinyl)-2-deoxyuridines (BVDU), salts thereof, protective forms thereof and prod rugs thereof can be used.

The at least one of a 5-substituted nucleoside and a prodrug thereof can comprise a prodrug of Formula (I).

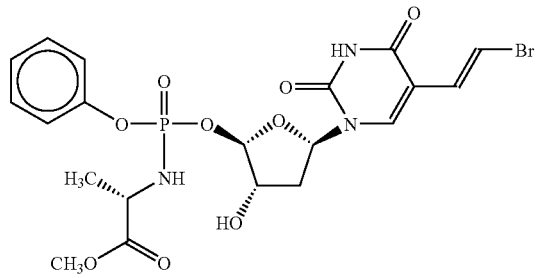

Formula 1

The at least one active substance can comprise at least one antibiotic.

The bacteria can be *Proteus* bacteria, *Escherichia coli*, *Streptococca* or *Staphylococca*.

The infectious disease can be caused by *Plasmodia*, and the at least one active substance can comprise at least one of antibiotics and anti-infective agents active against *Plasmodia*.

The infectious disease can be malaria, and the at least one active substance can comprise 4-aminoquinolines.

The at least one active substance can comprise quinine derivatives, and the quinine derivatives can be Chioroquine, Amodiaquine, mepacrine or Sontaquine.

The at least one active substance can comprise antifolates. The antifolates can be pyrimethamine, chloroguanide, sulphones or sulphonamides.

The infectious disease can comprise *Leishmaniases*, and the at least one active substance can comprise at least one of chemotherapeutics, antibiotics and anti-infectives.

The at least one active substance can comprise at least one chemotherapeutic, and the chemotherapeutic can comprise methotrexate.

The at least one of a 5-substituted nucleoside and a prodrug thereof can be used in concentrations such that a blood concentration of 0.01 to 10 μg/ml results.

The at least one of a 5-substituted nucleoside and a prodrug thereof can be used in concentrations such that a blood concentration of 0.05 to 5 µg/ml results.

The at least one active substance can be used in a therapeutic concentration.

The administering can comprise administration by at least one of injection, orally, rectally, intravaginally, intranasally and local application.

The method can further comprise administering additives comprising at least one of aqueous and non-aqueous solvents, stabilizers, suspension agents, dispersion agents and wetting agents.

The method can further comprise administering additives comprising at least one of polyethylene glycols, colourants and perfume agents.

The at least one of a 5-substituted nucleoside and a prodrug thereof and the at least one active substance can be in the form of a fine powder, powder, suspension, solution, emulsion, salve or paste.

BRIEF DESCRIPTION OF THE DRAWINGS

The present invention is further described in the detailed description which follows, in reference to the noted drawing by way of a non-limiting exemplary embodiment of the present invention, and wherein:

FIG. 10 shows BVDU alone.

DETAILED DESCRIPTION OF THE INVENTION AND EXAMPLES

Figure 1:
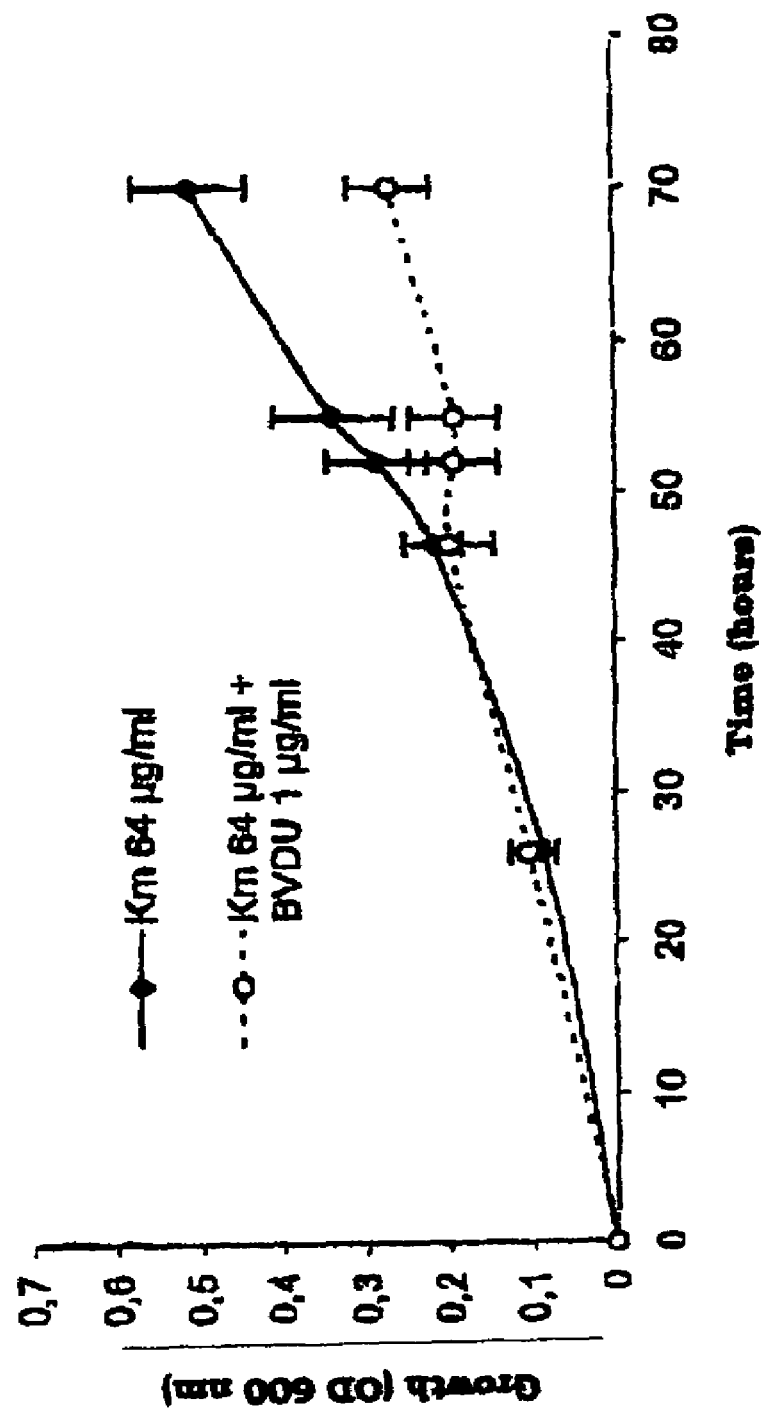
FIGS. 1 and 2 show the results of growth tests using Kanamycin and BVDU.

Resistance-free therapy of infectious diseases from the group of infections caused by bacteria or by protozoa is achieved in that, together with the substance which is active against the infectious disease, 5-substituted nucleosides and/or the prodrugs thereof are administered.

The active substance and the 5-substituted nucleosides or the prodrugs thereof can thereby occur both in a single formulation and in separate formulations as a combination preparation. A simultaneous, separate or temporally separated application can thereby occur.

Preferably, the 5-substituted nucleosides are selected from (E)-5-(2-bromovinyl)-2-deoxyuridines (BVDU), the salts thereof, the protective forms thereof and the prodrugs thereof. The compound of formula 1 can thereby be used preferably as prodrug.

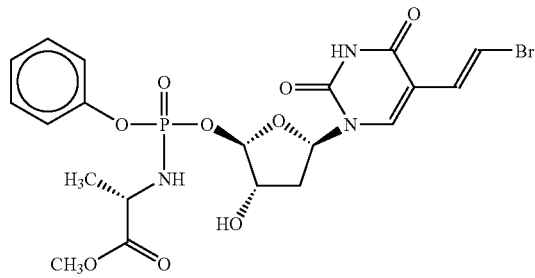

Formula 1

Antibiotics are used in a preferred embodiment as active substances for resistance-free therapy of bacterial infectious diseases. All bacteria indiscriminately are thereby possible as the bacteria triggering infection because of the proved importance of recombination in resistance development and because of the proved importance of gene amplification, e.g. *Proteus* bacteria, *Escherichia coli*, *Streptococca* and *Staphylococca*.

For the resistance-free therapy of malaria or of other infections caused by *Plasmodia*, antibiotics and/or anti-infectives, such as e.g. 4-aminoquinolines, are used as active substances. Chloroquine, Amodiaquine, mepacrine and Sontaquine are used particularly preferably thereby.

Antifolates are used as further preferred active substance against malaria or other infections caused by *Plasmodia*. For example, pyrimethamine, chloroguadine, sulphones and sulphonamides are included here.

For the resistance-free therapy of *Leishmaniases*, chemotherapeutics, antibiotics and/or anti-infectives are used preferably as active substances. Methotrexate is thereby used as preferred chemotherapeutic.

The 5-substituted nucleosides or the prodrugs thereof are used preferably in such concentrations that, after administration, a concentration of 5-substituted nucleosides or the prodrugs thereof in the blood of between 0.01 and 10 µg/ml, particularly preferred between 0.05 and 5 µg/ml, results.

The active substances are administered in standard concentrations according to the type of infectious disease, as are listed for example in current drug lists. Reference is made here in particular to the Red List 2001 (Red List Service GmbH, Frankfurt/Main).

Administration both of the active substances and also the 5-substituted nucleosides can be effected by injection, orally, rectally, intravaginally, intranasally and/or by local application.

In addition to the active substance and the 5-substituted nucleosides, there can also be used as further additives, aqueous and non-aqueous solvents, stabilizers, suspension agents, dispersion agents and wetting agents in the formulations. There are possible as additional additives, e.g. polyethylene glycols, colourants and perfume agents. The formulation can thereby be effected in the form of a fine powder, a powder, a suspension, a solution, an emulsion, a salve or a paste.

The subject according to the invention is now intended to be explained in more detail with reference to the following examples and FIGS. 1 to 10 without restricting the subject to these examples.

1. EXAMPLE

Prevention of Resistance Development in Bacteria

*Escherichia coli* J53 was used as Gram-negative model organism in order to test the effectiveness of BVDU. This organism carries the naturally occurring plasmid RP4, on which resistances to Ampicillin, Tetracycline and Kanamycin are encoded.

1.1 Adaptation to Kanamycin

Kanamycin is a naturally occurring aminoglycoside antibiotic. It is used for the treatment of bacterial infections, if it is not possible to use Penicillin or less toxic antibiotics. Fields of use are inter alia, infections of the bones, the respiratory tracts and of the skin and also complicated urinary tract infections and endocarditis.

Figure 2:
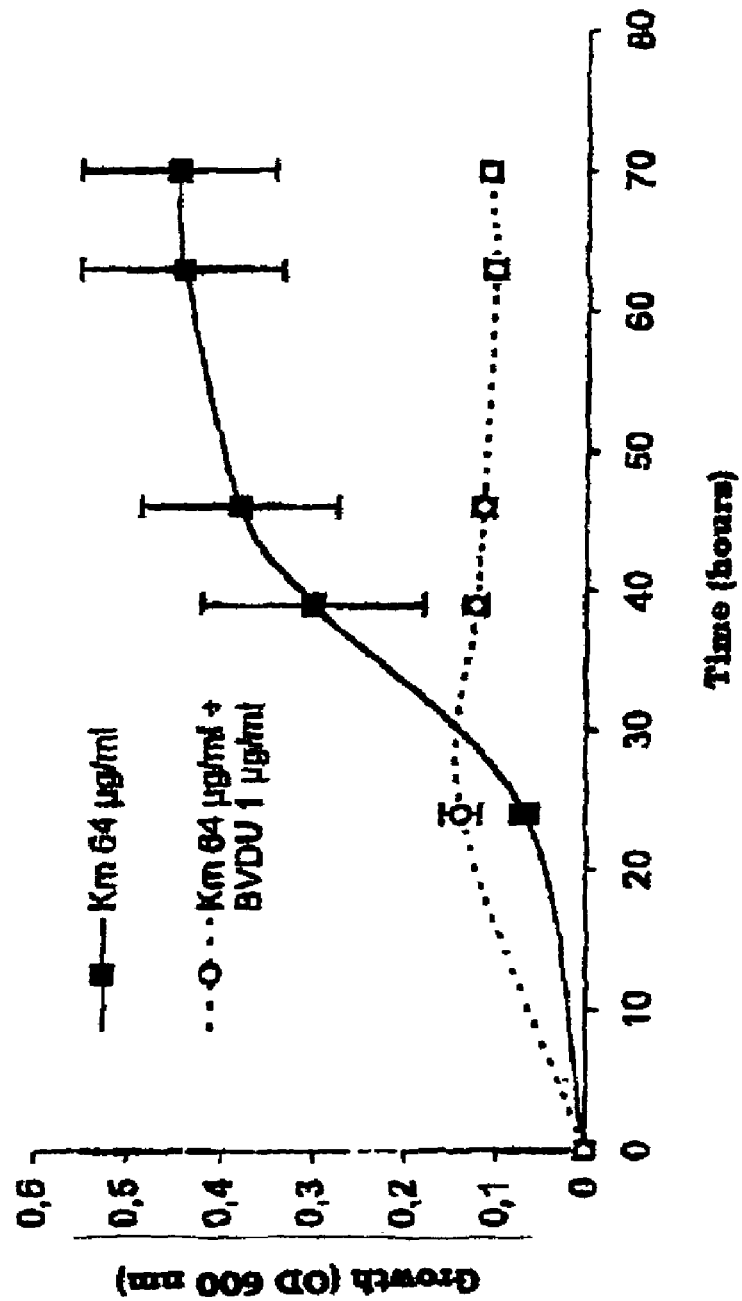

In growth tests with Kanamycin (64 µg/ml), a slow adaptation, i.e. resistance development, of *E. coli* J53 (RP4) to this concentration of the antibiotic was achieved. In the presence of BVDU (1 µg/ml), an inhibition of this resistance development/adaptation occurred. The results are illustrated in FIGS. 1 and 2.

The gradual adaptation to 64 µg/ml Kanamycin led to a stable change in the resistance spectrum relative to the antibiotic which was used.

Figure 3:
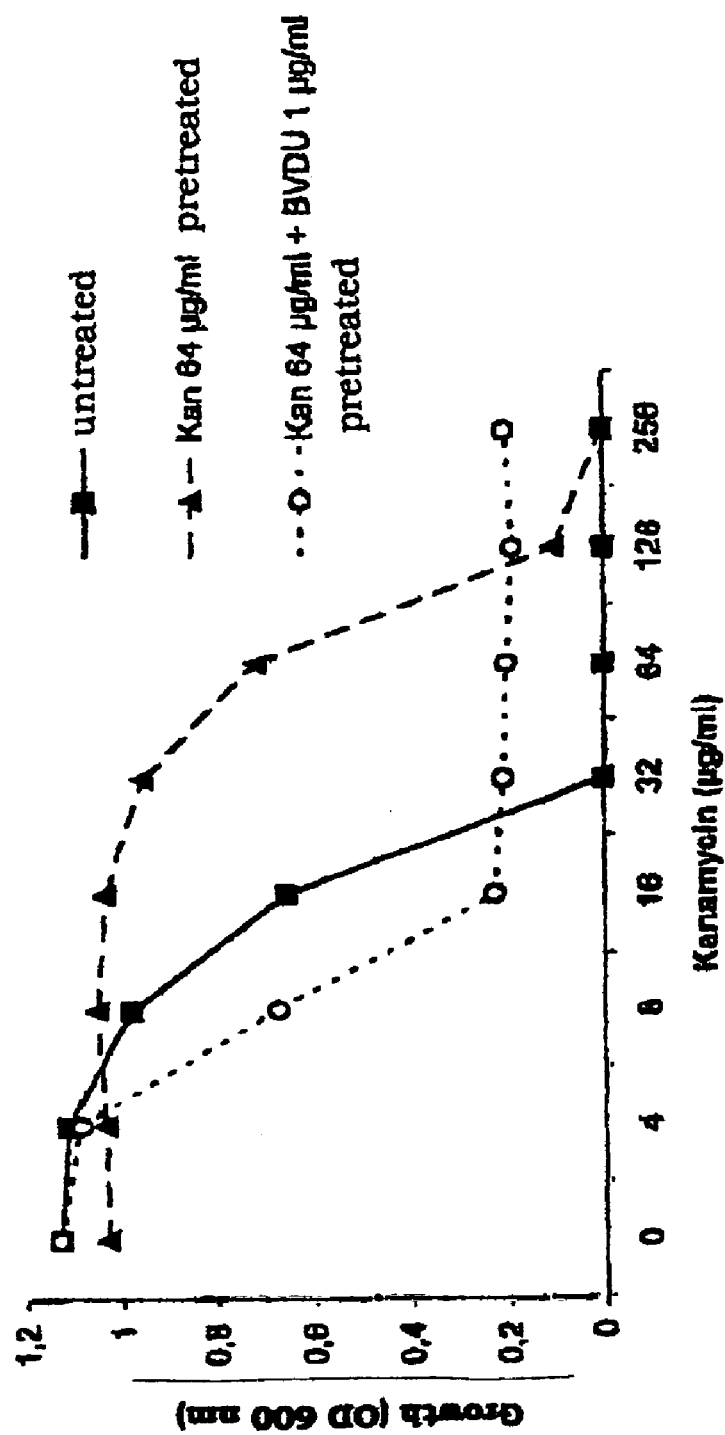
FIG. 3 shows comparison of MIC of Kanamycin.

In order to determine the minimal inhibitory concentrations (MIC), precultures were used initially for which antibiotic-free culture medium had been inoculated directly from frozen glycerine cultures. The strain, which had become resistant to 64 µg/ml Kanamycin had with 128 µg/ml a four times increased MIC relative to the starter strain (FIG. 3). The strain grown in the presence of 1 µg/ml BVDU, which had achieved no resistance to 64 µg/ml Kanamycin, showed growth inhibition already from 16 µg/ml Kanamycin. However even higher antibiotic concentrations still led to the growth of the inoculum. However, the growth inhibition prevented a larger cell density in the bacteria culture being reached.

Figure 4:
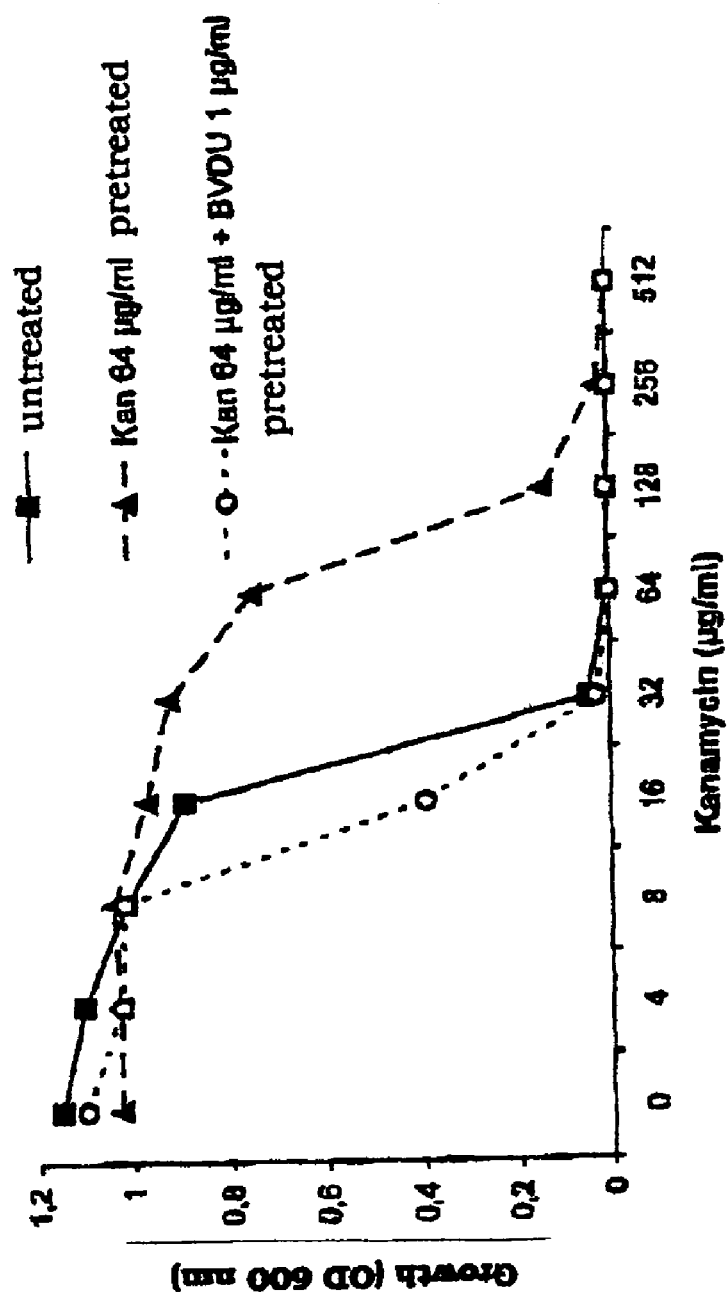
FIG. 4 shows comparison of MIC of Kanamycin.

In order to test the stability of the specific resistance features of the *E. coli* strains, the MIC determination was repeated. The already tested precultures were again absorbed for this purpose in antibiotic-free culture medium and tested for their Kanamycin resistance. The resistance spectra of the starter strain and of the strain adapted to 64 µg/ml remained unchanged. However, differences were revealed in the strain which was pretreated with 64 µg/ml Kanamycin +1 µg/ml BVDU. The growth of the inoculum was hereby completely prevented from a concentration of 32 µg/ml Kanamycin. The MIC of this strain corresponded hence to that of the starter strain. The results are illustrated in FIG. 4.

This means in summary that BVDU prevents the development of resistance to antibiotics and increases the sensitivity to antibiotics in a specific concentration range.

1.2 Adaptation to Amikacin

Amikacin acts against pathogens which are resistant to the remaining aminoglycosides. It is given in the case of severe infectious diseases of the kidneys, urinary and sexual organs and in infections of the respiratory tracts and of the gastrointestinal tract.

Figure 5:
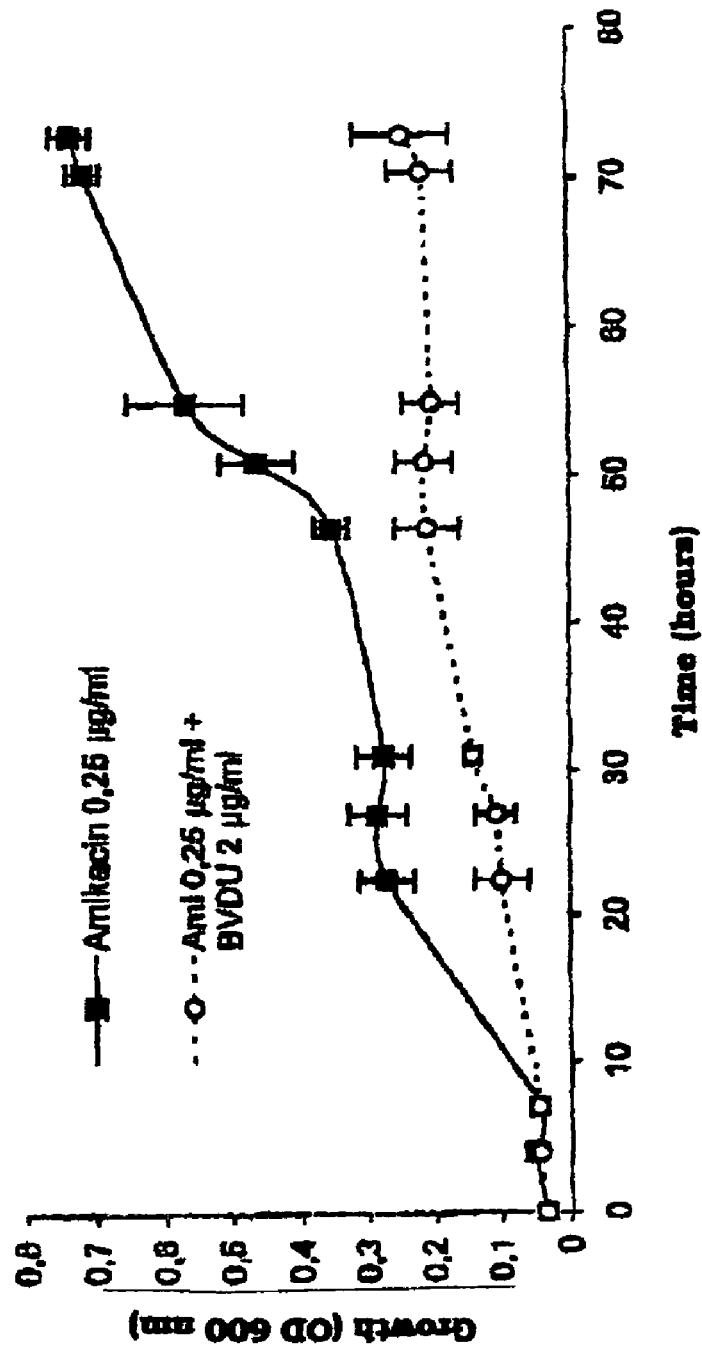
FIG. 5 shows the results of growth tests with Amikacin and BVDU.
Figure 6:
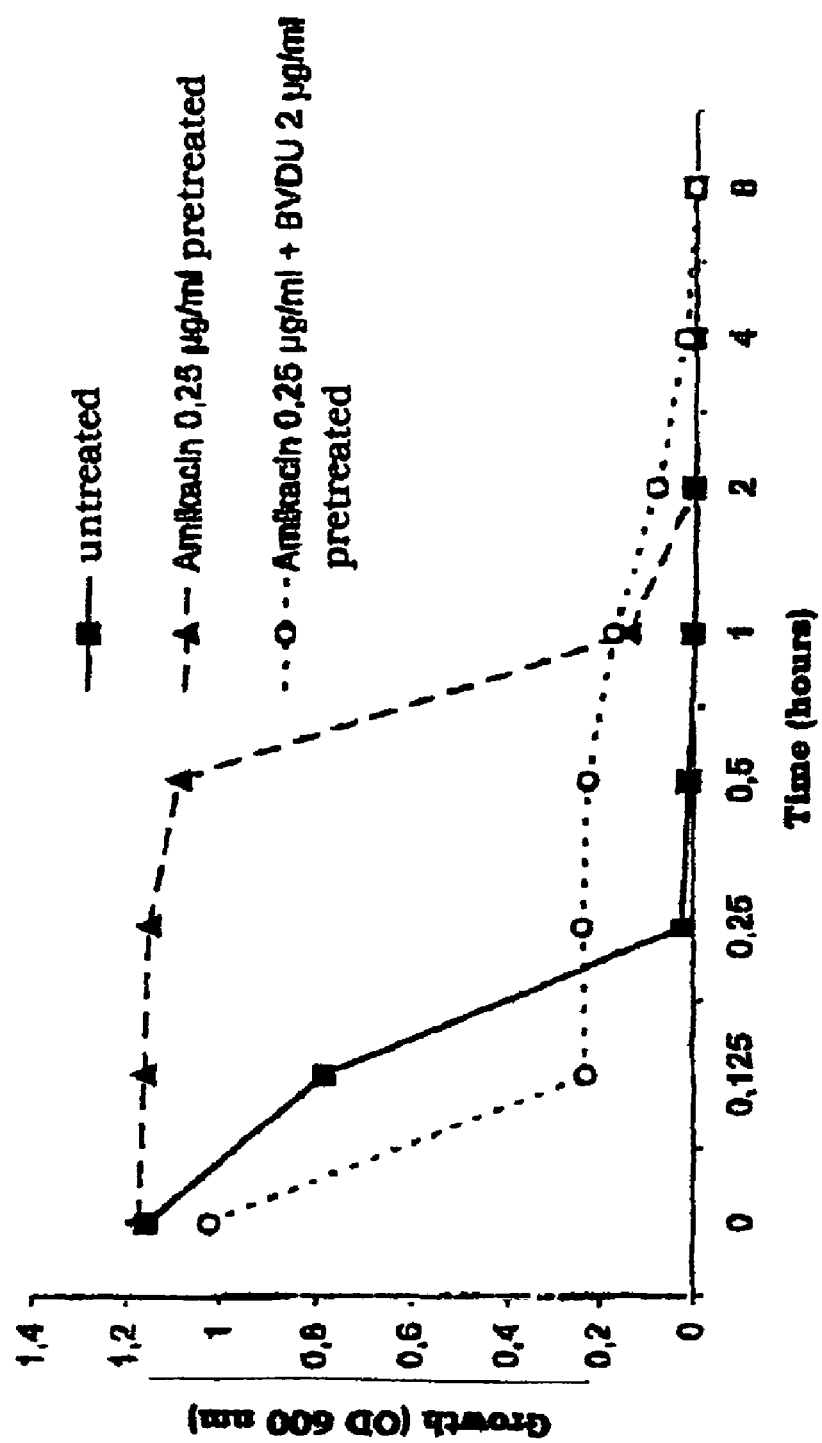
FIG. 6 shows comparison of MIC of Amikacin.

In growth tests with Amikacin (0.25 µg/ml), a slow adaptation, i.e. resistance development, of *E coli* J53 (RP4) to this concentration of the antibiotic was achieved. In the presence of BVDU (2 µg/ml), inhibition of this adaptation occurred (FIG. 5).

The gradual adaptation to 0.25 µg/ml Amikacin led to a stable change in the resistance spectrum relative to the antibiotic which was used.

The strain which had become resistant to 0.25 µg/ml Amikacin had with 2 µg/ml an eight times increased minimal inhibitory concentration (MIC) relative to the starter strain. The strain grown in the presence of 2 µg/ml BVDU which had achieved no resistance to 0.25 µg/ml Amikacin, showed growth inhibition already from 0.125 µg/ml Amikacin. This inhibition also prevented a larger cell density in the bacteria culture being reached with higher antibiotic concentrations. The results can be deduced from FIG. 6.

2. EXAMPLE

BVDU Conditioned Growth Inhibition After Aminoglycoside/BVDU Pretreatment

In order to determine the minimal inhibitory concentrations (MIC) of Kanamycin or Amikacin relative to aminoglycoside/BVDU-pretreated *E coli* J53 (RP4) strains, standard precultures were used which contained no additives in the culture medium (recovery phase). In addition, it was tested in comparative experiments to what extent the addition of BVDU to the antibiotic-free precultures changes the resistant spectrum of the strains.

Figure 7:
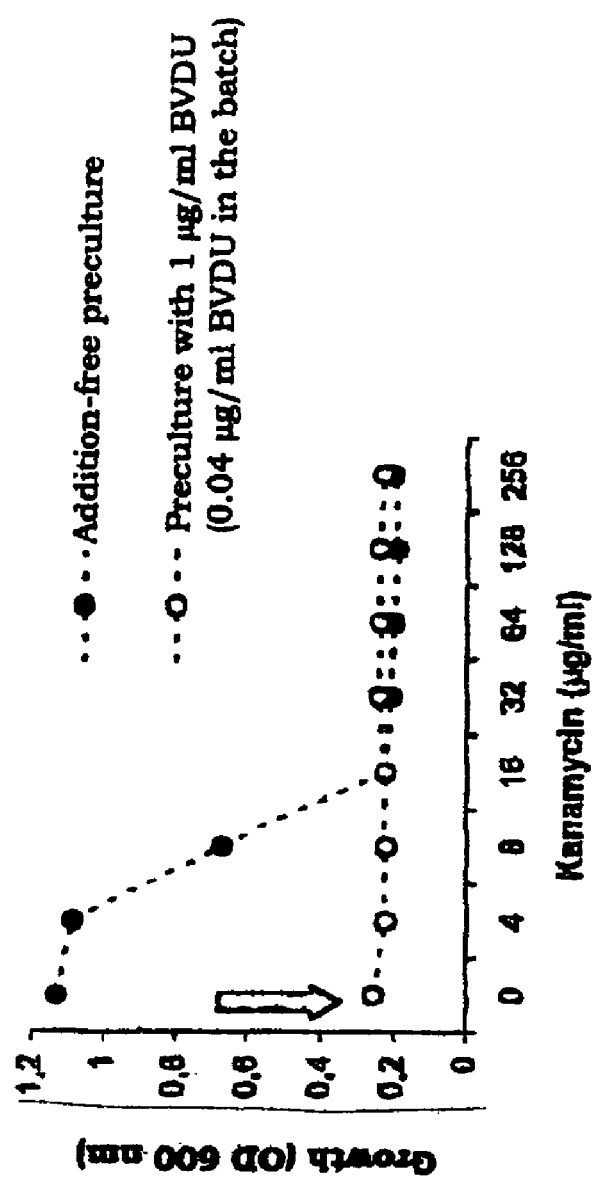
FIG. 7 shows determination of MIC of Kanamycin.
Figure 8:
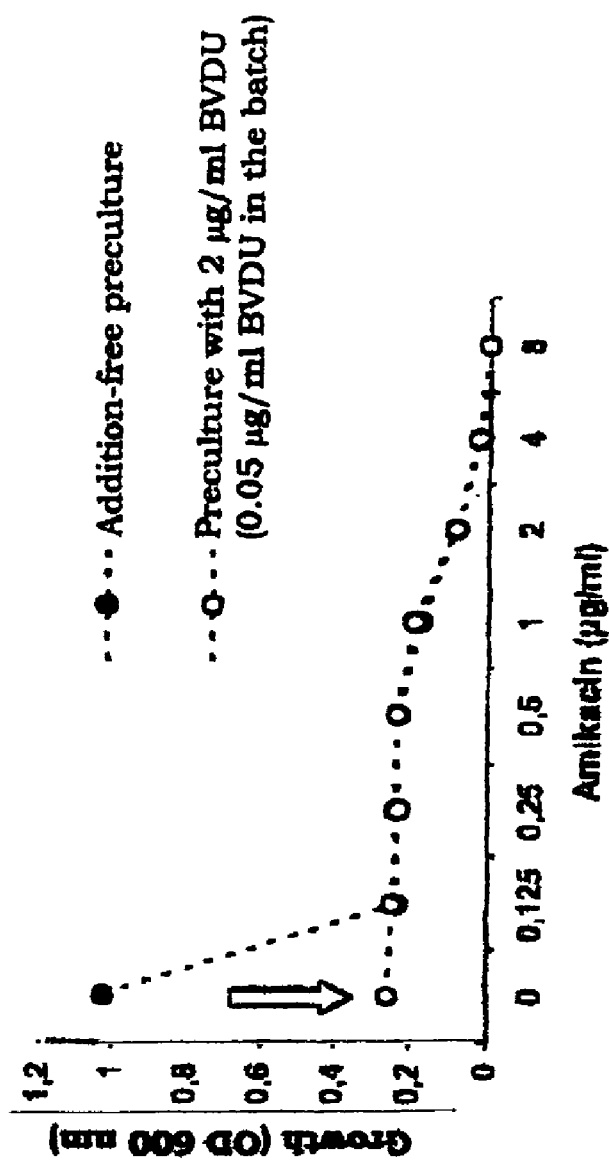
FIG. 8 shows comparison of MIC of Amikacin.
Figure 9:
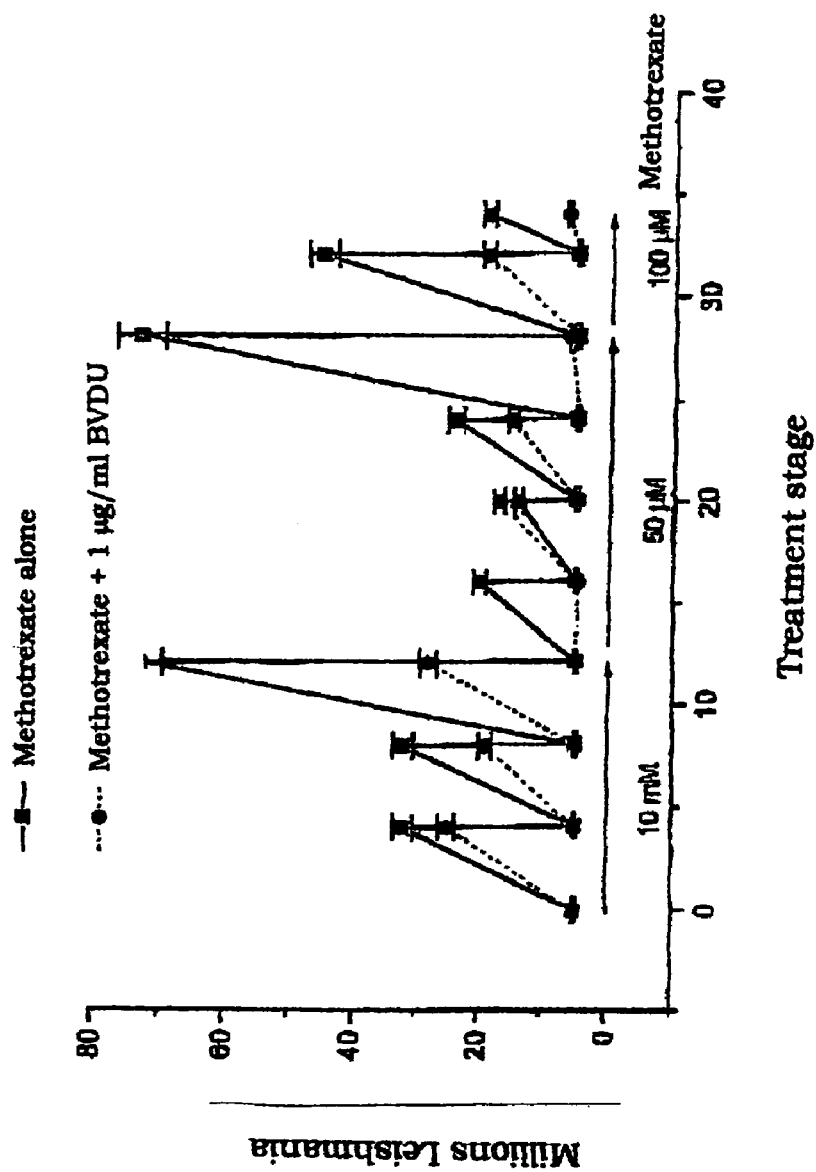
FIG. 9 shows the results of growth tests with methotrexate and BVDU.

The presence of BVDU (1 or 2 µg/ml) in the preculture or/and the small BVDU quantity (0.04–0.05 µg/ml) present due to transfer into the MIC batches sufficed for sustained restriction of the growth of aminoglycoside/BVDU-pretreated *E. coli* strains even in the absence of the antibiotic. In comparison therewith, the growth without antibiotic in the additive-free preculture corresponded to that of the untreated *E. coli* strain. The results are illustrated in FIGS. 7 and 8.

This implies in summary that BVDU also acts alone after removing an antibiotic. BVDU without pretreatment (antibiotic+BVDU) results in no effect and is not toxic.

3. EXAMPLE

Prevention of Resistance Development in Protozoa

Prevention of resistance development in Zooflagellates (*Leishmania*) by the simultaneous administration of the anti-recombinogenic 5-substituted nucleoside (E)-5-(2-bromovinyl)2'-deoxyuridines (BVDU) with methotrexate.

Protozoa of the Zooflagellata strain, such as e.g. *Trypanosoma* as pathogens of sleeping sickness and *Leishmania* (intracellular parasitic protozoa of the Mastigophora class) as pathogens of *Leishmniases* are infectious. Resistances to chemotherapy are based both in *Trypanosoma* (Wilson et al., 1991) and *Leishmania* (Ouellette and Borst, 1991; Grondin et al., 1998; Arana et al., 1998; Haimeur and Ouellette, 1998; Kundig et al., 1999) on the amplification of some genes which also play a role in the chemoresistance of tumours. The resistance development is intended to be prevented via the prevention of chemotherapy-induced recombination/gene amplification.

Methotrexate (MTX) resistant cells of *Leidshmania donovanii* were produced by gradual increase in the MTX concentrations of 5 to 10, of 10 to 50 and of 50 to 100 µm MTX. $5 \times 10^6$ cells/ml respectively were seeded in the growth medium. The cells were diluted again to $5 \times 10^6$ cells/ml for each new batch. The cells were then constantly subjected to the next higher MTX concentration when the cell division rate of the MTX-subjected cells had stabilised to the control level. This was possible after respectively approximately three to four passages. If 1 μg/ml BVDU was added simultaneously to the cultures, then the cell division rate never reached the control level, i.e. the cells developed, in contrast to the cells treated with MTX alone, no resistance to the treatment. The result of this test can be seen in a simplified version in FIGS. 9 and 10.

What is claimed is:

1. A method for the resistance-free therapeutic treatment of infectious disease caused by bacteria or protozoa selected from Gram-negative bacteria, *Trypanosoma* or *Leishmania*, comprising administering to an individual in need thereof at least one of (E)-5-(2-bromovinyl)-2-deoxyuridine (BVDU), salts thereof, protective forms thereof and prodrugs thereof together with at least one active substance selected from antibiotics and antiprotozoics.

2. The method according to claim 1 wherein the at least one of (E)-5-(2-bromovinyl)-2-deoxyuridine (BVDU), salts thereof, protective forms thereof and prodrugs thereof and the at least one active substance selected from antibiotics and antiprotozoics are present in a single formulation.

3. The method according to claim 1 wherein the at least one of (E)-5-(2-bromovinyl)-2-deoxyuridine (BVDU), salts thereof, protective forms thereof and prodrugs thereof and the active substance selected from antibiotics and antiprotozoics are present in separate formulations.

4. The method according to claim 1 wherein the at least one of (E)-5-(2-bromovinyl)-2-deoxyuridine Formula 1

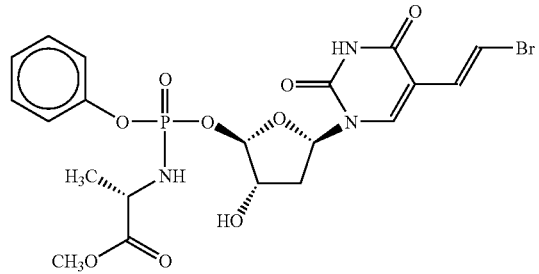

(BVDU), salts thereof, protective forms thereof and prodrugs thereof comprises a prodrug of Formula (I).

5. The method according to claim 1 wherein the at least one active substance selected from antibiotics and antiprotozoics comprises at least one antibiotic selected from aminoglycosides, beta lactames, tetracyclines and quinolones.

6. The method according to claim 1 wherein the at least one active substance selected from antibiotics and antiprotozoics comprises quinine derivatives, and the quinine derivatives are Chloroquine, Amodiaquine, mepacrine or Sontaquine.

7. The method according to claim 1 wherein the at least one active substance further includes antifolates.

8. The method according to claim 7 wherein the antifolates comprise pyrimethamine, chloroguanide, sulphones or sulphonamides.

9. The method according to claim 1 wherein the infectious disease comprises *Leishmaniases*.

10. The method according to claim 9 wherein the at least one active substance further includes at least one chemotherapeutic, and the chemotherapeutic comprises methotrexate.

11. The method according to claim 1 wherein the at least one of (E)-5-(2-bromovinyl)-2-deoxyuridine (BVDU), salts thereof, protective forms thereof and prodrugs thereof is used in concentrations such that a blood concentration of 0.01 to 10 μg/ml results.

12. The method according to claim 1 wherein the at least one of (E)-5-(2-bromovinyl)-2-deoxyuridine (BVDU), salts thereof, protective forms thereof and prodrugs thereof is used in concentrations such that a blood concentration of 0.05 to 5 μg/ml results.

13. The method according to claim 1 wherein the at least one active substance is used in a therapeutic concentration.

14. The method according to claim 1 wherein the administering comprises administration by at least one of injection, orally, rectally, intravaginally, intranasally and local application.

15. The method according to claim 1 further comprising administering additives comprising at least one of aqueous and non-aqueous solvents, stabilizers, suspension agents, dispersion agents and wetting agents.

16. The method according to claim 1 further comprising administering additives comprising at least one of polyethylene glycols, colourants and perfume agents.

17. The method according to claim 1 where the at least one of (E)-5-(2-bromovinyl)-2-deoxyuridine (BVDU), salts thereof, protective forms thereof and prodrugs thereof and the at least one active substance are in the form of a fine powder, powder, suspension, solution, emulsion, salve or paste.

18. The method according to claim 1 wherein the Gram-negative bacteria comprise *Esherichia coli*.

* * * * *